United States Patent
Yamamoto et al.

(10) Patent No.: US 11,168,882 B2
(45) Date of Patent: Nov. 9, 2021

(54) BEHAVIOR INDUCEMENT SYSTEM, BEHAVIOR INDUCEMENT METHOD AND RECORDING MEDIUM

(71) Applicant: PANASONIC INTELLECTUAL PROPERTY MANAGEMENT CO., LTD., Osaka (JP)

(72) Inventors: Yuka Yamamoto, Osaka (JP); Tomoko Takenaga, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 44 days.

(21) Appl. No.: 16/760,374

(22) PCT Filed: Oct. 23, 2018

(86) PCT No.: PCT/JP2018/039264
§ 371 (c)(1),
(2) Date: Apr. 29, 2020

(87) PCT Pub. No.: WO2019/087851
PCT Pub. Date: May 9, 2019

(65) Prior Publication Data
US 2021/0164644 A1    Jun. 3, 2021

(30) Foreign Application Priority Data

Nov. 1, 2017   (JP) .............................. JP2017-211969

(51) Int. Cl.
| | |
|---|---|
| *H04R 1/02* | (2006.01) |
| *F21V 33/00* | (2006.01) |
| *G16H 20/70* | (2018.01) |
| *G16Y 40/10* | (2020.01) |
| *G16Y 40/30* | (2020.01) |
| *G06F 3/16* | (2006.01) |
| *G16Y 10/80* | (2020.01) |

(52) U.S. Cl.
CPC .......... *F21V 33/0056* (2013.01); *G06F 3/165* (2013.01); *G16H 20/70* (2018.01);
(Continued)

(58) Field of Classification Search
CPC ....................................................... H04R 1/02
See application file for complete search history.

(56) References Cited

U.S. PATENT DOCUMENTS

| | | | |
|---|---|---|---|
| 6,725,064 B1 | 4/2004 | Wakamatsu et al. | |
| 2013/0132837 A1* | 5/2013 | Mead ................... | G06Q 20/123 715/716 |

(Continued)

FOREIGN PATENT DOCUMENTS

| | | |
|---|---|---|
| JP | H10-228228 A | 8/1998 |
| JP | 2002-236791 A | 8/2002 |

(Continued)

OTHER PUBLICATIONS

International Search Report and Written Opinion dated Nov. 27, 2018, in International Patent Application No. PCT/JP2018/039264; with partial English translation.

*Primary Examiner* — Olisa Anwah
(74) *Attorney, Agent, or Firm* — McDermott Will and Emery LLP

(57) ABSTRACT

A behavior inducement system includes: a communication unit which obtains information from a household device, an information communication device, and a behavior detector which detects a behavior; and a control unit which controls a lighting device having a music playback function based on the information obtained by the communication unit. The communication unit obtains, from the information communication device, inducement information indicating condition related to inducement, obtains, from the household device, household device information indicating a state of the household device, and obtains, from the behavior detector, behavior information indicating the behavior. The control unit causes the lighting device to start playback of music via the communication unit when the state satisfies the condition, and, based on the behavior information, the (Continued)

control unit adjusts, after the start of the playback of the music, time required for the lighting device to complete the playback of the music.

8 Claims, 4 Drawing Sheets

(52) U.S. Cl.
CPC .............. *G16Y 40/10* (2020.01); *G16Y 40/30* (2020.01); *H04R 1/028* (2013.01); *G16Y 10/80* (2020.01)

(56) References Cited

U.S. PATENT DOCUMENTS

| | | | | |
|---|---|---|---|---|
| 2014/0152181 A1* | 6/2014 | Burkhart | .............. | H05B 47/155 315/122 |
| 2015/0208489 A1* | 7/2015 | Dijk | .................... | H05B 47/175 315/294 |
| 2015/0332622 A1* | 11/2015 | Liu | ...................... | G09G 3/2003 705/14.54 |
| 2016/0153650 A1* | 6/2016 | Chien | ................. | F21V 33/0004 362/253 |
| 2016/0255437 A1* | 9/2016 | Wen | .......................... | F21K 9/23 381/300 |
| 2017/0048476 A1* | 2/2017 | Kapri | ............... | H04N 21/43615 |
| 2017/0177833 A1* | 6/2017 | Lewallen | ........... | G09B 19/0038 |
| 2017/0238401 A1* | 8/2017 | Sadwick | .............. | H05B 47/195 315/294 |
| 2018/0056202 A1* | 3/2018 | Michael | ............... | A63H 33/006 |
| 2018/0199414 A1* | 7/2018 | Zheng | ................... | H05B 47/19 |

FOREIGN PATENT DOCUMENTS

| | | |
|---|---|---|
| JP | 2003-204391 A | 7/2003 |
| JP | 2004-078304 A | 3/2004 |
| JP | 2011-017903 A | 1/2011 |
| JP | 2016-072013 A | 5/2016 |

\* cited by examiner

BEHAVIOR INDUCEMENT SYSTEM, BEHAVIOR INDUCEMENT METHOD AND RECORDING MEDIUM

CROSS-REFERENCE OF RELATED APPLICATIONS

This application is the U.S. National Phase under 35 U.S.C. § 371 of International Patent Application No. PCT/JP2018/039264, filed on Oct. 23, 2018, which in turn claims the benefit of Japanese Application No. 2017-211969, filed on Nov. 1, 2017, the entire disclosures of which Applications are incorporated by reference herein.

TECHNICAL FIELD

The present disclosure relates to a behavior inducement system, behavior inducement method and recording medium which induces a human behavior.

BACKGROUND ART

The number of dual-working families with children has increased following increasing entrance of women into the society in recent years. Moreover, women are in charge of housework and childcare following an increase in nuclear families in many cases, imposing great loads on the women. There have been demands for reducing the loads of childcare on the women under such condition.

For example, Patent Literature (PTL) 1 discloses an accident prevention system which is provided with means for recognizing a risk factor present in a monitor region and which detects approach of a baby or an infant to the risk factor, if any, and provides support information so that a caregiver of the baby or infant can take a behavior of keeping the baby or infant away from the risk factor.

With the conventional art disclosed in PTL 1, it is possible that upon the approach of the baby or infant to the risk factor, the support information is provided to the mother to support the mother to keep the baby or infant away from the risk factor or "discipline" the baby or infant so that the baby or infant can recognize the risk factor.

CITATION LIST

Patent Literature

PTL 1: Japanese Unexamined Patent Application Publication No. 2004-078304

SUMMARY OF THE INVENTION

Technical Problem

However, with the conventional art disclosed in PTL 1, the mother is required to take her time for disciplining the baby or infant. Thus, it is hard to say that the loads imposed on the mothers in double-work families are reduced.

Thus, the present disclosure provides a behavior inducement system, behavior inducement method and recording medium capable of leading a target person to voluntarily behave.

Solutions to Problem

A behavior inducement system according to one aspect of the present disclosure refers to a behavior inducement system that induces a human behavior, and includes: a communication unit configured to obtain information from a household device, an information communication device, and a behavior detector which detects the human behavior; and a control unit configured to control a lighting device having a music playback function based on the information obtained by the communication unit, wherein the communication unit is configured to obtain, from the information communication device, inducement information indicating condition related to the inducement, obtain, from the household device, household device information indicating a state of the household device, and obtain, from the behavior detector, behavior information indicating the human behavior, the control unit is configured to cause the lighting device to start playback of music via the communication unit when the state indicated in the household device information obtained by the communication unit satisfies the condition indicated in the inducement information obtained by the communication unit, and based on the behavior information obtained by the communication unit, the control unit is configured to adjust, after the start of the playback of the music, time required for the lighting device to complete the playback of the music.

Moreover, a behavior inducement method according to another aspect of the present disclosure refers to a behavior inducement method for inducing a human behavior, and the behavior inducement method includes: obtaining information from a household device, an information communication device, and a behavior detector which detects the human behavior; and controlling a lighting device having a music playback function based on the information obtained, wherein in the obtaining the information, inducement information indicating condition related to the inducement is obtained from the information communication device, household device information indicating a state of the household device is obtained from the household device, and behavior information indicating the human behavior is obtained from the behavior detector, and the controlling includes: causing the lighting device to start playback of music through communication when the state indicated in the household device information obtained satisfies the condition indicated in the inducement information obtained; and based on the behavior information obtained, adjusting, after the start of the playback of the music, time required for the lighting device to complete the playback of the music.

Moreover, a recording medium according to still another aspect of the present disclosure is a non-transitory, computer-readable recording medium having recorded thereon a program causing a computer to execute the behavior inducement method described above.

Advantageous Effect of Invention

The present disclosure can provide a behavior inducement system, behavior inducement method and recording medium capable of leading a target person to voluntarily behave.

DESCRIPTION OF EXEMPLARY EMBODIMENT

Hereinafter, an embodiment of the present disclosure will be described in detail with reference to the drawings.

Note that the embodiment described below illustrates a comprehensive or detailed example. Numerical values, shapes, components, and arrangement positions and connection modes of the components as well as steps and a sequence of the steps illustrated in the embodiment below form one example and are not intended to limit the present disclosure in any manner. Moreover, of the components in the embodiment described below, those not described in an independent claim indicating the most generic concept of the present disclosure will be described as optional components. Moreover, each figure does not necessarily provide precise illustration. Substantially same configurations in each figure are provided with same reference marks and description thereof will be omitted or simplified.

Embodiment

[Outline of Behavior Inducement System]

Figure 1:
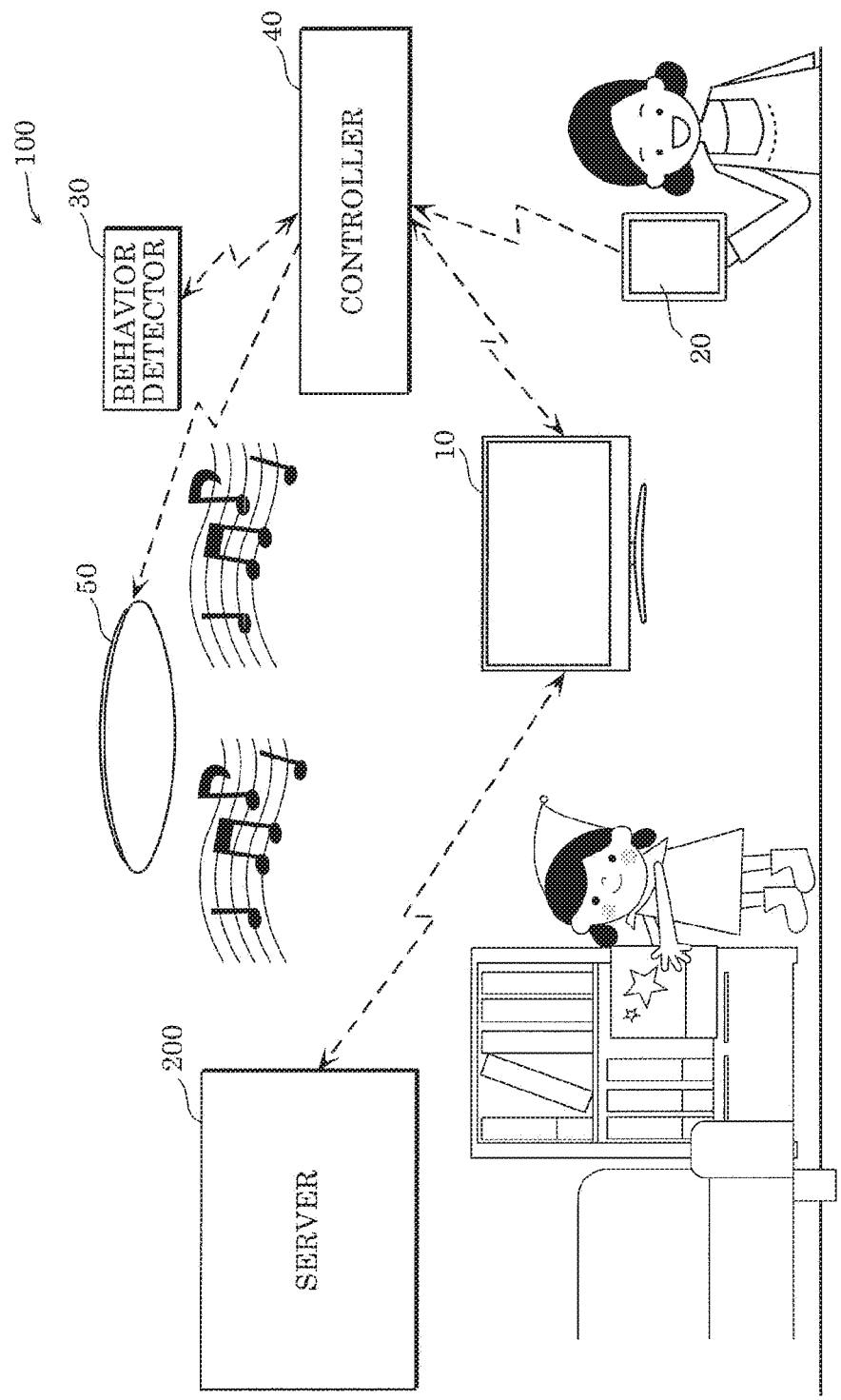
FIG. 1 is a diagram illustrating an outline of a behavior inducement system according to an embodiment.

FIG. 1 is a diagram illustrating an outline of behavior inducement system 100 according to the present embodiment.

Behavior inducement system 100 according to the present embodiment is a system which induces a human behavior and which controls indoor environment by lighting device 50 having a music playback function (hereinafter simply referred to as "lighting device 50") to permit a human to voluntarily behave.

Behavior inducement system 100 includes: household device 10, information communication device 20, behavior detector 30, controller 40, and lighting device 50. Note that behavior inducement system 100 may or may not include server 200.

Household device 10 is a device which is arranged in a house, and a television is illustrated here as an example. Information communication device 20 is a device which transmits inducement information to controller 40, and a smartphone is illustrated here as an example. Behavior detector 30 is a device which detects human movement, and a camera is illustrated here as an example.

Note that the inducement information is condition related to inducement and includes here: timing information for inducing a human behavior; and behavior inducement program information indicating an inducement method. The timing information refers to, for example, timing at which controller 40 starts the control of lighting device 50 based on a predetermined behavior inducement program. The behavior inducement program information is, for example, program information for controlling lighting operation and music playback performed by lighting device 50.

Moreover, the human is a target person whose behavior is to be induced, and an infant is illustrated here as an example. Moreover, the behavior refers to a target behavior induced by behavior inducement system 100, for example, cleanup, preparing the next day's belongings, preparing the table, changing clothes, or preparing for bed. Illustrated here is an example in which the infant is induced to perform cleanup.

Hereinafter, the outline of behavior inducement system 100 according to the present embodiment will be described with reference to FIG. 1. Behavior inducement system 100 is, for example, a system which induces infant's behavior. More specifically, behavior inducement system 100 is a system in which, at timing at which the infant has completed viewing a TV program, controller 40 controls lighting device 50 to execute indoor lighting operation and music playback, thereby leading the infant to notice that now is time to perform cleanup so that the infant can voluntarily perform cleanup. Note that a detailed example illustrated in FIG. 1 is just one example, and behavior inducement system 100 of the present disclosure is not limited to such an example.

Controller 40 is connected to television 10, smartphone 20, camera 30, and lighting device 50. Controller 40 may be independently arranged or may be incorporated in lighting device 50. Further, television 10 is connected to server 200. Television 10 downloads data from server 200. Server 200 stores data such as TV program information and TV program content information. The aforementioned connections may be wired or wireless.

A mother can previously input the inducement information with smartphone 20 and make settings for operating lighting device 50 at predetermined timing and by a program. Note that the predetermined timing and the program will be described later on in section "Configuration of Behavior Inducement System".

[Configuration of Behavior Inducement System]

Figure 2:
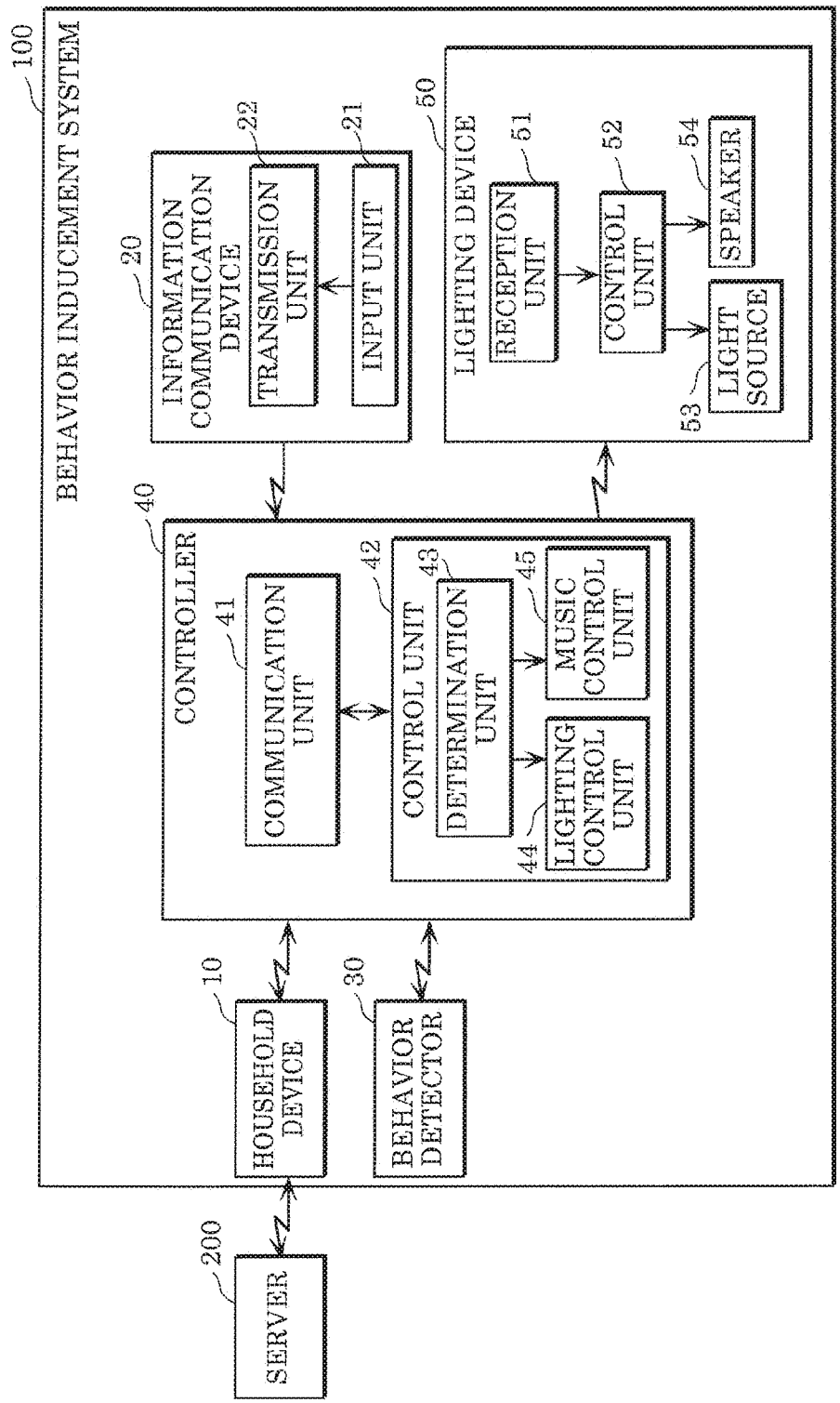
FIG. 2 is a functional block diagram illustrating a configuration of the behavior inducement system according to the embodiment.

Hereinafter, the configuration of behavior inducement system 100 according to the present embodiment will be described. FIG. 2 is a functional block diagram illustrating the configuration of behavior inducement system 100 according to the present embodiment.

As illustrated in FIG. 2, behavior inducement system 100 includes household device 10, information communication device 20, behavior detector 30, controller 40, and lighting device 50.

Household device 10 is a device which is arranged in a house. Household device 10 is, for example, a television, a game machine, or a moving image playback device. Household device 10 is connected to server 200 and controller 40. Household device 10 downloads data from server 200. The data here refers to, for example, data of a TV program table or program contents in a case where household device 10 is a television and refers to data of game software, etc. in a case where household device 10 is a game machine.

Household device 10 transmits household device information to controller 40. The household device information is information indicating the state of household device 10 and indicates a human behavior of household device 10. For example, in a case where household device 10 is a television, the household device information is information indicating a playback state of television 10, for example, whether television 10 is playing back a predetermined program or has just completed the playback of the predetermined program.

Information communication device 20 transmits the inducement information to controller 40. Information communication device 20 is, for example, a smartphone, a tablet terminal, or a personal computer, and includes input unit 21 and transmission unit 22. Input unit 21 is, for example, a touch panel, a keyboard, a mouse, or a microphone.

Information communication device 20 is connected to controller 40 via transmission unit 22. Transmission unit 22 is a wireless communication interface such as Bluetooth (registered trademark), IrDA, or Wi-Fi (registered trademark). Note that transmission unit 22 may be a wired communication interface such as Ethernet (registered trademark).

Behavior detector 30 detects a human behavior and transmits behavior information indicating the human behavior to controller 40. Upon the detection of the human behavior, human movement itself may be detected or movement of an object moved by the human movement may be detected. That is, the behavior information may be information indicating the human movement or may be information indicating the movement of the object moved by the human movement.

Behavior detector 30 is, for example, a camera or a sensor. In a case where behavior detector 30 is a camera, behavior detector 30 may detect infant's movement of cleaning up a toy, a picture book, or the like and may attach a tag to the toy, the picture book, or the like to detect the movement of the toy, the picture book, or the like cleaned up by the infant. In a case where behavior detector 30 is a sensor, behavior detector 30 may measure a weight change with a weight sensor incorporated in a storage container, for example, a toy box, to thereby detect the movement of the toy, the picture book, or the like cleaned up by the infant.

Note that behavior detector 30 may be connected to controller 40 wirelessly or with a wire. Moreover, behavior detector 30 may be independently arranged or may be incorporated in lighting device 50.

Controller 40 controls indoor environment. The indoor environment in the present embodiment is, for example, visual environment and auditory environment. Controller 40 may be installed on the ceiling or a wall or may be incorporated in lighting device 50. Controller 40 includes communication unit 41 and control unit 42.

Communication unit 41 obtains information from household device 10, information communication device 20, and behavior detector 30. More specifically, communication unit 41 obtains the inducement information indicating the condition related to the inducement from information communication device 20, obtains the household device information indicating the state of household device 10 from household device 10, and obtains the behavior information indicating the human behavior from behavior detector 30. Communication unit 41 is a wireless communication interface such as Bluetooth (registered trademark), IrDA, or Wi-Fi (registered trademark). Note that communication unit 41 may be a wired communication interface such as Ethernet (registered trademark).

Control unit 42 controls lighting device 50 based on the information obtained by communication unit 41. Control unit 42 includes a central processing unit (CPU) and a ROM and a RAM storing programs, and is provided with determination unit 43, lighting control unit 44, and music control unit 45. Note that determination unit 43, lighting control unit 44, and music control unit 45 are realized by executing the programs by the CPU.

When the state indicated in the household device information obtained by communication unit 41 satisfies the condition indicated in the inducement information obtained by communication unit 41, control unit 42 causes lighting device 50 to start the playback of music via communication unit 41, and based on the behavior information obtained by communication unit 41, performs control of adjusting, after the start of the playback of the music, time required for lighting device 50 to complete the playback of the music.

Determination unit 43 determines whether or not the state indicated in the household device information obtained by communication unit 41 satisfies the condition indicated in the inducement information obtained by communication unit 41. Here, the condition indicated in the inducement information includes, for example, timing information for activating the behavior inducement program which induces a human behavior (hereinafter may be simply referred to as "timing information"), which is timing information for causing controller 40 to start the control of lighting device 50 based on a predetermined behavior inducement program. The aforementioned information is, for example, timing information for starting the control of the lighting device in which controller 40 transmits a control command to lighting device 50 "when the state of household device 10 has turned into a predetermined state".

Lighting control unit 44 transmits, to lighting device 50 via communication unit 41, a signal for controlling light source 53 of lighting device 50.

Music control unit 45 transmits, to lighting device 50 via communication unit 41, a signal for controlling speaker 54 of lighting device 50.

Lighting device 50 is a lighting device having the music playback function and includes reception 51, control unit 52, light source 53, and speaker 54. Reception unit 51 receives signals from controller 40. Control unit 52 controls light source 53 and speaker 54 based on the received signals. Reception unit 51 is a wireless communication interface such as a Bluetooth (registered trademark), IrDA, or Wi-Fi (registered trademark). Note that reception unit 51 may be a wired communication interface such as Ethernet (registered trademark). Control unit 52 includes, for example, a processor, and a ROM and a RAM storing programs. Light source 53 is, for example, a light-emitting diode (LED).

[Operation of Behavior Inducement System]

Figure 3:
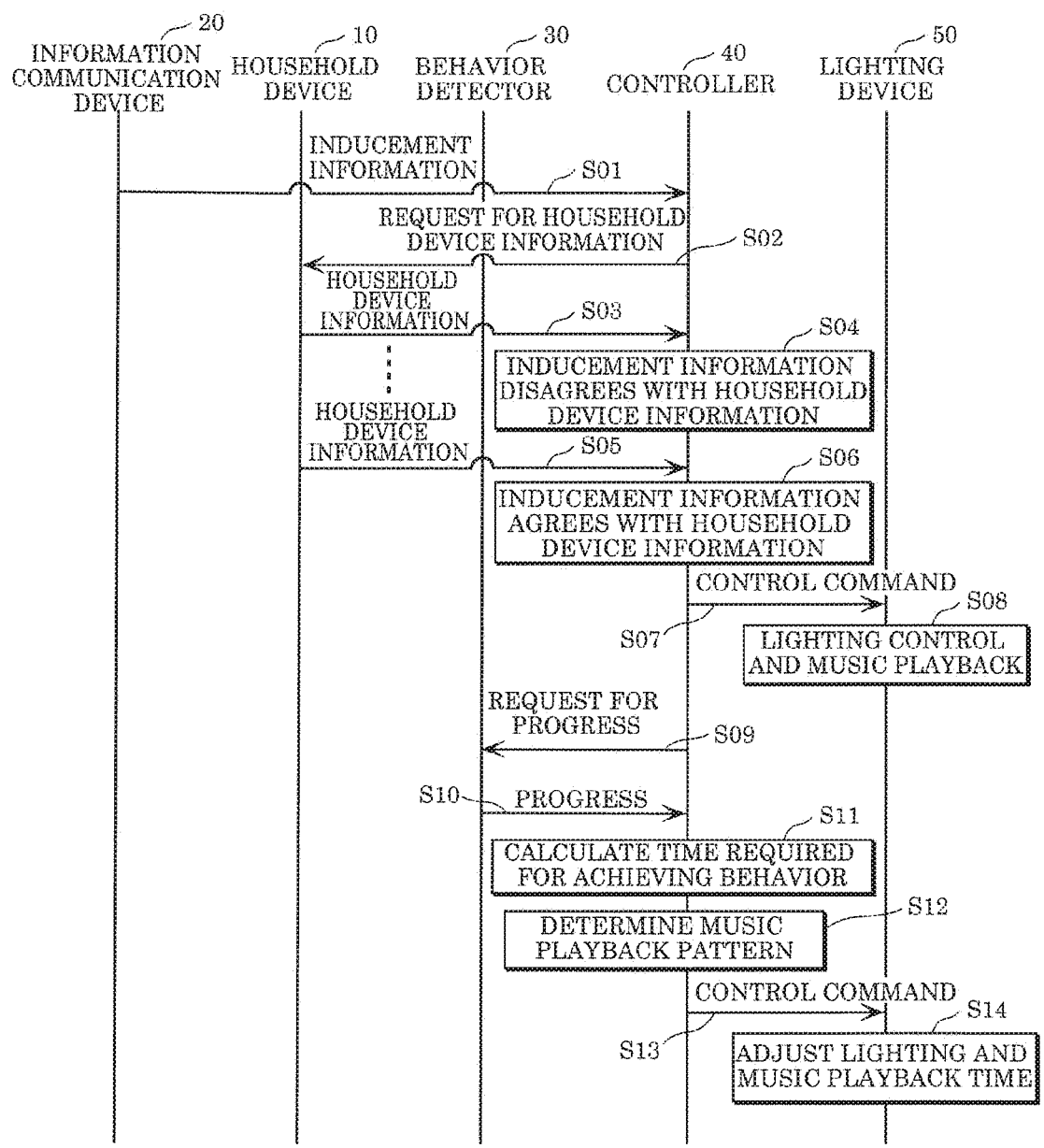
FIG. 3 is a sequence diagram illustrating an operation example of the behavior inducement system according to the embodiment.

Next, the operation of behavior inducement system 100 according to the present embodiment will be described. FIG. 3 is a sequence diagram illustrating an operation example of behavior inducement system 100 according to the present embodiment.

Here, a person whose behavior is to be induced is an infant and the behavior induced is cleaning up, for example, a toy. Moreover, information communication device 20 is a smartphone of infant's mother, household device 10 is a television, and behavior detector 30 is a camera.

As illustrated in FIG. 3, in behavior inducement system 100, the mother first previously selects, by using smartphone 20, timing information such as "when television 10 has completed the playback of a predetermined TV program" and program information for executing lighting operation and music playback and transmits the aforementioned information as the inducement information to controller 40. For example, the mother can previously set the inducement information for inducing infant's behavior, for example, the mother can select, as the timing information, "when television 10 has completed the playback of a given animation program" and can select, as the program information, "the white level of the lighting is increased to brighten the room and also music preferred by the infant is played for ten minutes". The setting of the inducement information may be performed every time the infant's behavior is to be induced or may be regularly repeated with a day and time set.

Upon obtaining the inducement information from smartphone 20 (step S01), controller 40 requests television 10 for the household device information (step S02). Television 10 transmits, as the household device information to controller 40, a predetermined TV program, that is, a fact that the TV program set as the timing information by the mother is being played back (step S03). Upon obtaining the household device information from television 10, controller 40 determines whether or not the timing information indicated in the inducement information set by the mother agrees with the household device information. At this point, the timing information is set as "when television 10 has completed the playback of a predetermined TV program", and the household device information is set as "television 10 is playing back the predetermined TV program". Thus, controller 40 determines that "the timing information indicated in the inducement information set by the mother disagrees with the household device information". As described above, when the timing information indicated in the inducement information disagree with the household device information (step S04), controller 40 requests television 10 for the household device information again (step S02). Note that steps S02 and S03 are repeated until the timing information indicated in the inducement information agrees with the household device information. Then upon ending of the predetermined TV program, television 10 transmits, as the household device information to controller 40, a fact that the predetermined program has ended (step S05).

Upon obtaining the household device information from television 10, controller 40 determines whether or not the timing information indicated in the inducement information set by the mother agrees with the household device information indicating the state of household device 10. At this point, the timing information is "television 10 has completed the playback of a predetermined TV program" and the household device information is "television 10 has completed the playback of the predetermined TV program". Thus, controller 40 determines that "the timing information indicated in the inducement information set by the mother agrees with the household device information". As described above, when the timing information indicated in the inducement information agrees with the household device information (step S06), controller 40 transmits a command for stopping the transmission of the household device information to television 10. Then controller 40 transmits, to lighting device 50, a control command for executing the lighting operation and the music playback (step S07). Note that controller 40 may request camera 30 for image data indicating a current status at this point. Consequently, the indoor status upon the initial start of the behavior inducement program and the achievement status of cleanup after passage of predetermined time can be compared with each other as, for example, a level of messiness, which therefore makes it possible to more accurately predict time required for achieving the aforementioned behavior.

When lighting device 50 receives the control command transmitted from controller 40, lighting device 50 executes the behavior inducement program regarding lighting operation and music playback, in accordance with the control command (step S08). Upon passage of the predetermined time from when lighting device 50 starts the execution of the behavior inducement program, controller 40 requests camera 30 for the image data indicating the progress of the cleanup (step S09). Camera 30 transmits the image data indicating the progress to controller 40 (step S10), upon which controller 40 calculates time required for achieving the aforementioned behavior (step S11). Note that achieving the behavior refers to completing the induced behavior, i.e., completing the cleanup here. At this point, controller 40 calculates the progress based on the obtained image data, i.e., the level of messiness upon passage of the predetermined time since the start of the cleanup. Then the level of messiness after the passage of the predetermined time is compared with the indoor status at time of the start of the behavior inducement program, that is, the level of messiness at the time of the start of the cleanup to calculate time required for completing the cleanup. Here, the level of messiness is calculated, for example, as described below. A tag or the like is provided to a toy, a picture book, or the like and a state of the room is photographed with camera 10. Based on the photographed image, the number of tags present in the room is identified, and the number of tags in the room at the time of the start of the cleanup and the number of tags in the room after passage of the predetermined time since the start of the cleanup are calculated. Then a difference between the aforementioned two numbers is calculated and the difference is divided by the passage time to calculate a speed of the cleanup performed by the infant. Based on the calculated cleanup speed, time required for completing the cleanup is calculated. Then in view of possibility that the cleanup speed changes, the predetermined time is added to the calculated time required for completing the cleanup to calculate the time required for completing the cleanup.

Controller 40 calculates a difference between the calculated time required for completing the cleanup and time (ten minutes) set by the behavior inducement program and determines a music playback pattern based on a length of difference time (step S12). The music playback pattern may be a pattern which delays a music playback speed or may be a pattern in which part of the music, for example, a most popular portion is repeated. Adjustment for extending the preset time (ten minutes) may be made so that the infant does not notice this adjustment and the music playback pattern may be determined as appropriate based on the length of the difference time.

Upon determination of the music playback pattern, controller 40 transmits a control command to lighting device 50 (step S13). For example, assumed at this point is that the set time is ten minutes and the difference time is five minutes. Controller 40 determines that it is better to repeat the most popular portion than to delay the music playback speed for the purpose of extending the set time in a manner such that the infant does not notice the extension, and transmits a control command for repeating the most popular portion to lighting device 50. Note that a lighting control command for, for example, maintaining the room bright by increasing the white level of the lighting until completion of the music playback is also transmitted together with the control commands for the music playback pattern and the playback time in step S13.

Upon receiving the control commands from controller 40, lighting device 50 makes adjustment of the lighting and music playback time (step S14). Consequently, the infant can feel the sense of achievement that he or she could perform cleanup during the playback of predetermined music, so that upon the playback of the predetermined music, the infant notices that it is time to perform cleanup and voluntarily engage himself or herself in the cleanup.

[Operation of Each Configuration of Controller]

Figure 4:
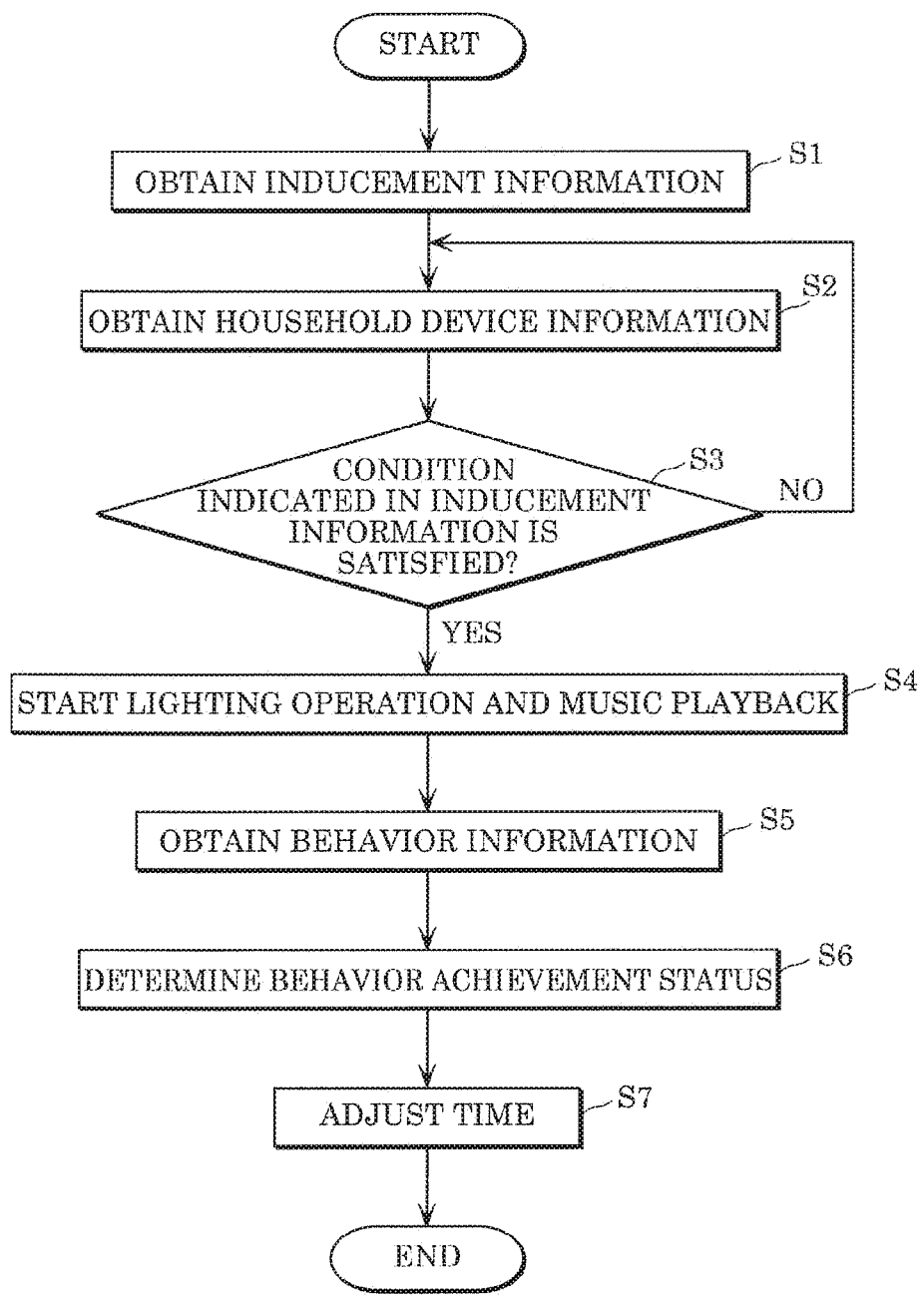
FIG. 4 is a flowchart illustrating an operation example of a communication unit and a control unit in the embodiment.

Next, the operation of each configuration of controller 40 according to the present embodiment will be described in more detail. FIG. 4 is a flowchart illustrating an operation example of communication unit 41 and control unit 42 of controller 40 according to the present embodiment.

Control unit 42 according to the present embodiment obtains the inducement information from information communication device 20 via communication unit 41 (step S1). Next, control unit 42 requests household device 10 for the household device information and obtains the household device information from household device 10 (step S2). Next, determination unit 43 in control unit 42 determines whether or not the state indicated in the household device information obtained from household device 10 satisfies the condition indicated in the inducement information obtained from information communication device 20 (step S3). That is, determination unit 43 determines whether or not the timing information indicated in the inducement information obtained from information communication device 20 agrees with the household device information indicating the state of household device 10.

Upon determination by determination unit 43 that the timing information agrees with the household device information (YES in step S3), lighting control unit 44 and music control unit 45 transmit a command for controlling the lighting and music playback to lighting device 50 via communication unit 41, causing the lighting operation and the music playback to be started (step S4). Note that upon determination by determination unit 43 that the timing information disagrees with the household device information (NO in step S3), control unit 42 requests household device 10 for the household device information and obtains the household device information from household device 10 (step S2). Then determination unit 43 determines whether or not the condition indicated in the inducement information obtained from information communication device 20 is satisfied (step S3).

After passage of the predetermined time after the start of the lighting operation and the music playback, control unit 42 obtains the behavior information from behavior detector 30 via communication unit 41 (step S5). At this point, the behavior information may be obtained by requesting behavior detector 30 for the behavior information by control unit 42 or the behavior information may be obtained without requesting behavior detector 30 for the behavior information by control unit 42. Next, based on the behavior information obtained by communication unit 41, determination unit 43 determines the achievement status of the human behavior (step S6). Based on the achievement status of the human behavior, music control unit 45 adjusts time so that lighting device 50 completes the playback of the music (step S7). At this point, music control unit 45 may adjust the time by adjusting the music playback speed or may adjust the time by repeatedly playing back at least part of the music. Consequently, a target person whose behavior is to be induced can complete the behavior during the music playback and thus can obtain the sense of achievement.

Note that not only the music but also the lighting may be controlled in step S7. Consequently, the target person whose behavior is to be induced can also visually recognize timing at which the next behavior is to be started, which therefore makes it possible to effectively induce the behavior of the person.

As described above, behavior inducement system 100 according to the present embodiment induces a human behavior. Behavior inducement system 100 includes: communication unit 41 which obtains information from household device 10, information communication device 20, and behavior detector 30 which detects the human behavior; and control unit 42 which controls lighting device 50 having the music playback function based on the information obtained by communication unit 41. Communication unit 41 obtains the inducement information indicating the condition related to the inducement from information communication device 20, obtains the household device information indicating the state of household device 10 from household device 10, and obtains the behavior information indicating the human behavior from camera 30. When the state indicated in the household device information obtained by communication unit 41 satisfies the condition indicated in the inducement information obtained by communication unit 41, control unit 42 causes lighting device 50 having the music playback function to start the playback of the music via communication unit 41 and based on the behavior information obtained by communication unit 41, adjusts, after the start of the playback of the music, three required for lighting device 50 having the music playback function to complete the playback of the music.

As described above, when the state indicated in the household device information satisfies the condition indicated in the inducement information, that is, when the timing information indicated in the inducement information agrees with the household device information indicating the state of the household device, a target person can recognize, as a result of the start of the playback of the music, that it is time to shift to the next behavior. For example, in a case where the timing information is "when a given TV program has ended" and the household device information is "when the television has ended the playback of the given TV program", control unit 42 determines that the state indicated in the household device information satisfies the condition indicated in the inducement information. Then since the music is played back at timing at which the target person has ended viewing the TV program, the target person can recognize that time to shift to the next behavior has come. At this point, the desire to view the TV program is being satisfied; therefore, the target person can easily switch his or her mind to engage himself or herself in the next behavior. Moreover, after the start of the playback of the music, time required for completing the behavior of the target person is calculated based on the behavior information of the target person, that is, the progress of the human behavior and time for playing back the music is adjusted in accordance with the time required for completing the behavior, which therefore makes it possible for the target person to complete the behavior during the music playback. Thus, the target person can get the sense of achievement that he or she could complete the behavior during the music playback. Consequently, the target person can get motivation to achieve the behavior during the music playback even from the next time. Therefore, with the behavior inducement system of the present disclosure, the target person can voluntarily behave.

Moreover, in behavior inducement system 100 according to the present embodiment, control unit 42 may determine the achievement status of the human behavior based on the behavior information obtained by communication unit 41 and may adjust the time based on the achievement status determined. More specifically, based on the behavior information, control unit 42 may predict timing at which the human behavior is to be achieved and completed and may adjust the time so that lighting device 50 having the music playback function completes the playback of the music at the predicted timing.

Consequently, the target person can complete the behavior during the music playback and thus can obtain the sense of achievement.

Moreover, control unit 42 may adjust the music playback speed to thereby adjust the time in behavior inducement system 100 according to the present embodiment.

Consequently, the target person can complete the behavior during the music playback and thus can obtain the sense of achievement.

Moreover, control unit 42 may repeatedly play back at least part of the music to thereby adjust the time in behavior inducement system 100 according to the present embodiment.

Consequently, the target person can complete the behavior during the music playback and thus can obtain the sense of achievement.

Moreover, in behavior inducement system 100 according to the present embodiment, control unit 42 may further control the lighting operation performed by lighting device 50 having the music playback function via communication unit 41 when the state indicated in the household device information obtained by communication unit 41 satisfies the condition indicated in the inducement information obtained by communication unit 41.

Consequently, the target person can also visually recognize timing at which the next behavior starts, which can therefore effectively induce the behavior of the target person.

Moreover, a behavior inducement method according to the present embodiment is a method for inducing a human behavior and includes: obtaining information from household device 10, information communication device 20, and behavior detector 30 which detects the human behavior; and controlling lighting device 50 having the music playback function based on the information obtained. In the obtaining the information, inducement information indicating condition related to inducement is obtained from the information communication device, household device information indicating the state of household device 10 is obtained from household device 10, and behavior information indicating the human behavior is obtained from behavior detector 30. The controlling includes: causing lighting device 50 having the music playback function to start the playback of music when the state indicated in the household device information obtained satisfies the condition indicated in the inducement information obtained; and based on the behavior information obtained, adjusting, after the start of the playback of the music, time required for lighting device 50 having the music playback function to complete the playback of the music.

Consequently, when the state indicated in the household device information satisfies the condition indicated in the inducement information, that is, when the timing information indicated in the inducement information agrees with the household device information indicating the state of the household device, as a result of the start of playback of the music, the target person can recognize that time to shift to the next behavior has come. For example, in a case where the timing information is "when a given TV program has ended" and the household device information is "the TV has just completed the playback of the given TV program", control unit 42 determines that the state indicated in the household device information satisfies the condition indicated in the inducement information. Then since the music is played back at timing at which the target person has ended viewing the TV program, the target person can recognize that the time to shift to the next behavior had come. The desire of the target person to watch the TV program is being satisfied at this point, which therefore makes it easier for the target person to switch his or her feeling to engage himself or herself in the next behavior. Moreover, after the start of the playback of the music, the time required for the target person to complete the behavior is calculated based on the behavior information of the target person, that is, the progress of the behavior, and the music playback time is adjusted in accordance with the time required for completing the behavior, which therefore makes it possible for the target person to complete the behavior during the music playback. Thus, the target person can obtain the sense of achievement that he or she could complete the behavior during the music playback. Consequently, the target person can have motivation to achieve the behavior during the music playback even from the next time. Therefore, with the behavior inducement method of the present disclosure, the target person can voluntarily behave.

Note that the aforementioned integrated or detailed modes may be realized in a system, a method, an integrated circuit, a computer program, or a computer-readable recording medium such as CD-ROM or may be realized by a desired combination of the system, the method, the integrated circuit, the computer program, and the recording medium.

Moreover, the control unit is realized by a software program in the embodiment described above but may be realized by dedicated hardware.

The behavior inducement system, the behavior inducement method, and the recording medium according to the present disclosure have been described above based on the embodiment, but the present disclosure is not limited to the aforementioned embodiment. Those obtained by making various modifications conceivable by those skilled in the art to the embodiment and another mode formed by combining part of the components in the embodiment are also included in the scope of the present disclosure.

Note that the television has been illustrated as an example of household device 10 in the present embodiment, but household device 10 may be a game machine. In this case, game software may be downloaded via the Internet or recorded onto a recording medium. A program may be incorporated as the household device information into the game software to transmit the progress of a game to controller 40.

Consequently, controller 40 can induce a behavior while determining, based on the progress of the game, the timing at which the behavior inducement program is activated, and thus can induce the infant to perform the next behavior when the game has settled down once. Thus, the desire of the infant is being satisfied, which therefore makes it easier for the infant to switch his or her feeling to engage himself or herself in the next behavior.

Moreover, the example of cleanup has been illustrated as the behavior to be induced in the present embodiment but the behavior to be induced may be going to bed. In this case, control of darkening lighting and control of reducing a sound volume of music may be performed with passage of time.

Consequently, the target person can also visually and auditorily recognize timing at which the next behavior is started, which therefore makes it possible to induce the behavior of the target person.

Moreover, behavior detector 30 operates after the start of the behavior inducement program in the present embodiment, but the behavior of the target person, for example, the infant in the present embodiment before the behavior inducement may be sensed. For example, how the infant watches a TV program or a DVD is photographed by camera 30. Then upon determination that the infant is fed up with the TV program or the DVD, a behavior inducement program for cleanup may be started. Examples of cases where it is determined that the infant is fed up with the TV program or the like include: a case where the number of times and a period for which the visual line of the infant is out of a TV screen has increased; a case where the body of the infant is oriented in a direction different from a direction of television 10; a case where a behavior of going to take another object such as a toy, a picture book, or the like has been observed; and a case where the number of times of blinking has increased.

As described above, in a case where the infant becomes fed up with a behavior which has been continuously performed, it is possible to effectively induce the next behavior.

The invention claimed is:

1. A behavior inducement system that induces a human behavior, the behavior inducement system comprising:
   a communication unit configured to obtain information from a household device, an information communication device, and a behavior detector which detects the human behavior; and
   a control unit configured to control a lighting device having a music playback function based on the information obtained by the communication unit, wherein
   the communication unit is configured to obtain, from the information communication device, inducement information indicating condition related to the inducement, obtain, from the household device, household device information indicating a state of the household device, and obtain, from the behavior detector, behavior information indicating the human behavior,
   the control unit is configured to cause the lighting device to start playback of music via the communication unit when the state indicated in the household device information obtained by the communication unit satisfies the condition indicated in the inducement information obtained by the communication unit, and
   based on the behavior information obtained by the communication unit, the control unit is configured to adjust, after the start of the playback of the music, time required for the lighting device to complete the playback of the music.

2. The behavior inducement system according to claim 1, wherein
   the control unit is configured to determine an achievement status of the human behavior based on the behavior information obtained by the communication unit and adjust the time based on the achievement status determined.

3. The behavior inducement system according to claim 2, wherein
   based on the behavior information, the control unit is configured to predict timing at which the human behavior is to be achieved and completed and adjust the time to cause the lighting device to complete the playback of the music at the timing predicted.

4. The behavior inducement system according to claim 1, wherein
   the control unit is configured to adjust the time by adjusting a speed of the playback of the music.

5. The behavior inducement system according to claim 1, wherein
   the control unit is configured to adjust the time by causing at least part of the music to be played back repeatedly.

6. The behavior inducement system according to claim 1, wherein
   when the state indicated in the household device information obtained by the communication unit satisfies the condition indicated in the inducement information obtained by the communication unit, the control unit is configured to further control lighting operation performed by the lighting device via the communication unit.

7. A behavior inducement method for inducing a human behavior, the behavior inducement method comprising:
   obtaining information from a household device, an information communication device, and a behavior detector which detects the human behavior; and
   controlling a lighting device having a music playback function based on the information obtained, wherein
   in the obtaining the information, inducement information indicating condition related to the inducement is obtained from the information communication device, household device information indicating a state of the household device is obtained from the household device, and behavior information indicating the human behavior is obtained from the behavior detector, and
   the controlling includes:
   causing the lighting device to start playback of music through communication when the state indicated in the household device information obtained satisfies the condition indicated in the inducement information obtained; and
   based on the behavior information obtained, adjusting, after the start of the playback of the music, time required for the lighting device to complete the playback of the music.

8. A non-transitory, computer-readable recording medium having recorded thereon a program causing a computer to execute the behavior inducement method according to claim 7.

* * * * *